US012709750B2

(12) United States Patent
Ishikawa et al.

(10) Patent No.: US 12,709,750 B2

(45) Date of Patent: Aug. 18, 2026

(54) AGENT FOR PREVENTING OR TREATING MUSCULAR DISEASE

(71) Applicant: TANABE PHARMA CORPORATION, Osaka (JP)

(72) Inventors: Kiyoshi Ishikawa, Osaka (JP); Shumpei Murata, Osaka (JP)

(73) Assignee: TANABE PHARMA CORPORATION, Osaka (JP)

( * ) Notice: Subject to any disclaimer, the term of this patent is extended or adjusted under 35 U.S.C. 154(b) by 756 days.

(21) Appl. No.: 18/005,520

(22) PCT Filed: Jul. 16, 2021

(86) PCT No.: PCT/JP2021/026798

§ 371 (c)(1),
(2) Date: Jan. 13, 2023

(87) PCT Pub. No.: WO2022/014703

PCT Pub. Date: Jan. 20, 2022

(65) Prior Publication Data

US 2023/0272386 A1 Aug. 31, 2023

(30) Foreign Application Priority Data

Jul. 17, 2020 (JP) ................................ 2020-122975
Feb. 19, 2021 (JP) ................................ 2021-025158

(51) Int. Cl.
*C12N 15/113* (2010.01)
*A61K 31/713* (2006.01)
*A61P 21/00* (2006.01)

(52) U.S. Cl.
CPC .......... *C12N 15/113* (2013.01); *A61K 31/713* (2013.01); *A61P 21/00* (2018.01); *C12N 2310/14* (2013.01)

(58) Field of Classification Search
CPC .............. C12N 15/113; C12N 2310/14; C12N 2310/11; A61K 31/713; A61K 31/7088; A61P 21/00
See application file for complete search history.

(56) References Cited

U.S. PATENT DOCUMENTS

2011/0281787 A1 11/2011 Lu et al.
2016/0228502 A1 8/2016 Desmond et al.
2017/0298107 A1 10/2017 Olson et al.

FOREIGN PATENT DOCUMENTS

CN 103079597 A 5/2013
JP 2017-21 4337 A 12/2017

OTHER PUBLICATIONS

Chen, R. et. al., Acta Physiologica, vol. 228, Issue 2, p. 1-13, Jul. 31, 2019. (Year: 2019).*

Anderson, D., et. al., Cell, vol. 160, p. 595-606, Feb. 12, 2015 (Year: 2015).*

Bennett, C., Annual Review of Medicine, vol. 70, p. 307-321, Jan. 2019 (Year: 2019).*

Agrawal et al., (2018) "Role of defective Ca2+signaling in skeletal muscle weakness: Pharmacological implications", Journal of Cell Communication and Signaling, 12(4):645-659.

Chen et al., (2019) "Primary Active Ca 2+ Transport Systems in Health and Disease", Cold Spring Harbor Perspectives in Biology, 12(2): a035113.

Ferreira et al., (2019) "LIM and cysteine-rich domains 1 (LMCD1) regulates skeletal muscle hypertrophy, calcium handling, and force", Skeletal Muscle, 9(1).

Mercuri et al., (2019) "Muscular dystrophies", The Lancet, 394(10213):2025-2038.

Molenaar et al., (2020) "Clinical, morphological and genetic Characterization of Brody disease: an international study of 40 patients", Brain, 143(2):452-466.

Extended European Search Report dated Jul. 29, 2025, issued in corresponding European Patent Application No. 21842938.9 (12 pages).

Sandonà et al., (2009) "Sarcoglycanopathies: molecular pathogenesis and therapeutic prospects", Expert Reviews in Molecular Medicine, vol. 11.

Tonkin et al., (2015) "One Small Step for Muscle: A New Micropeptide Regulates Performance", Cell Metabolism, 21(4):515-516.

Voit et al., (2017) "Reducing sarcolipin expression mitigates Duchenne muscular dystrophy and associated cardiomyopathy in mice", Nature Communications, 8(1).

International Search Report issued Sep. 21, 2021 in PCT/JP2021/026798 filed Jul. 16, 2021, 3 pages.

Roberts, N. et al., "Biochemical and Functional Comparisons of mdx and Sgcg$^{-/-}$ Muscular Dystrophy Mouse Models", *BioMed Research International*, Jan. 13, 2015, vol. 2015, 12 total pages.

Mazala, D. et al., "SERCA1 overexpression minimizes skeletal muscle damage in dystrophic mouse models", *Am J Physiol Cell Physiol*, Feb. 4, 2015, vol. 308, 11 pages.

Goonasekera, S. et al., "Mitigation of muscular dystrophy in mice by SERCA overexpression in skeletal muscle", *The Journal of Clinical Investigation*, Mar. 2011, vol. 121, No. 3, 10 pages.

Anderson, D. et al., "A Micropeptide Encoded by a Putative Long Noncoding RNA Regulates Muscle Performance", *Cell*, 2015, vol. 160, 13 pages.

Morine, K. et al., "Overexpression of SERCA1a in the mdx Diaphragm Reduces Susceptibility to Contraction-Induced Damage", *Human Gene Therapy*, Dec. 2010, vol. 21, 5 pages.

* cited by examiner

*Primary Examiner* — Neil P Hammell
*Assistant Examiner* — Krishna N Ravindra
(74) *Attorney, Agent, or Firm* — Finnegan, Henderson, Farabow, Garrett & Dunner, LLP

(57) ABSTRACT

A myoregulin inhibitor such as an antisense oligonucleotide against myoregulin or an anti-myoregulin antibody is used as an active ingredient of a prophylactic or therapeutic agent for a muscle disease such as muscular dystrophy, inclusion body myositis, amyotrophic lateral sclerosis, disused muscular atrophy, and sarcopenia.

20 Claims, 4 Drawing Sheets

Specification includes a Sequence Listing.

Mean ± S.E.M. n=4. ***$P$<0.0005, vs.vehicle (Williams' multiple comparison test)

Mean ± S.E.M. n=4. $P$<0.005, *$P$<0.0005 vs.vehicle (Williams' multiple comparison test)

Mean ± S.E.M. n=4. *$P$<0.025, ***$P$<0.0005 vs.vehicle (Williams' multiple comparison test)

Mean ± S.E.M. n=15. ***$P$<0.001 vs. Negative Control (Student's $t$-test)

AGENT FOR PREVENTING OR TREATING MUSCULAR DISEASE

CROSS-REFERENCE TO RELATED APPLICATIONS

This application is a national stage application of International Application No. PCT/JP2021/026798, filed Jul. 16, 2021, which is based upon and claims the benefit of priorities to Japanese Patent Applications No. 2021-025158, filed Feb. 19, 2021 and No. 2020-122975, filed Jul. 17, 2020. The entire contents of these applications are incorporated herein by reference.

TECHNICAL FIELD

The present invention relates to an agent for preventing or treating a muscle disease.

TECHNICAL BACKGROUND

A dystrophin-glycoprotein complex (DGC) is responsible for linking between a skeletal muscle and an extracellular matrix. DGC is formed of proteins such as dystrophin, sarcoglycan, and dystroglycan. When any of the above proteins that form DGC is deficient due to a gene mutation, a muscular dystrophy develops. A type lacking dystrophin is called Duchenne muscular dystrophy (DMD). DMD is the most frequently occurring muscular dystrophy and occurs in boys with an approximate frequency of 1 in 3,000. DMD is a severe type of muscular dystrophy, and a patient becomes non-ambulatory around the age of 10 and becomes wheelchair-bound. When abnormal expression of dystrophin is mild, symptoms are milder than those of DMD, and such a pathological condition is called Becker muscular dystrophy (BMD). Types lacking sarcoglycan are classified into 2C-2F types of limb-girdle muscular dystrophy (LGMD), collectively called sarcoglycanopathies. Sarcoglycanopathies are also severe types, many of which show clinical symptoms similar to DMD.

For muscular dystrophy caused by deficiency of proteins that form DGC, it is considered that occurrence of an abnormality in intracellular calcium regulation is one of causes of disease progression (Non-Patent Document 1). For DMD, it has been reported that, in a skeletal muscle of a model mouse of DMD, when expression of Sarcoplasmic/Endoplasmic Reticulum Calcium ATPase (SERCA) 1 is increased, a muscular dystrophy ameliorates (Non-Patent Document 2). Similarly, it has been clarified that, also in a sarcoglycanopathy model mouse, due to increased expression of SERCA1, a muscular dystrophy ameliorates (Non-Patent Document 3). SERCAs are proteins that are localized in an endoplasmic reticulum membrane and contribute to regulation of intracellular calcium levels by playing a role of a pump that takes in calcium from cytoplasm into endoplasmic reticulum, and among them, SERCA1 is a type that is specifically expressed in a skeletal muscle.

From the above, it is suggested that, for muscular dystrophy caused by deficiency of proteins that form DGC, an increase in SERCA1 activity leads to amelioration of a muscular dystrophy. Further, also for other muscle diseases in which an abnormality occurs in calcium regulation, an increase in SERCA1 activity may lead to amelioration of a pathological condition. However, no compound has been reported that can sufficiently selectively increase SERCA1 activity.

Myoregulin (MRLN) has been discovered as a micropeptide that is encoded by a long noncoding RNA, is specifically expressed in a skeletal muscle, and regulates calcium in sarcoplasmic reticulum by suppressing SERCA activity. It has been reported that an MRLN-deficient mouse has increased sarcoplasmic reticulum calcium level and exercise capacity, and it is suggested that a mechanism thereof is due to release of suppression of SERCA1 (Non-Patent Document 4). However, the mouse used in this document is a wild-type mouse lacking MRLN and does not reflect a pathological condition of a muscle disease. It has also been reported that expression of SERCA1 is decreased in a DMD model mouse (mdx mouse), and even when SERCA1 activity is increased by regulating MRLN expression in a state of a muscle disease, whether a muscle disease ameliorates is unclear (Non-Patent Literature 5).

In this way, although a relationship between MRLN and SERCA1 has been reported, a relationship between suppression of MRLN expression and a muscle disease such as muscular dystrophy has not been reported.

RELATED ART

Non-Patent Documents

[Non-Patent Document 1] Biomed Res Int., 2015: 131436 (2015)

[Non-Patent Document 2] Am J Physiol Cell Physiol., 308 (9): C699-709

[Non-Patent Document 3] J Clin Invest., 121 (3): 1044-52 (2011)

[Non-Patent Document 4] Cell, 160 (4): 595-606 (2015)

[Non-Patent Document 5] HUMAN GENE THERAPY, 21: 1735-1739 (2010)

SUMMARY OF THE INVENTION

Problems to be Solved by the Invention

An object of the present invention is to provide a agent for treating or preventing a muscle disease such as muscular dystrophy.

Means for Solving the Problems

As a result of intensive studies, the present inventors have found that an MRLN inhibitor is effective for treating or preventing a muscle disease, and thus have accomplished the present invention.

A summary of the present invention is as follows.

[1] A prophylactic or therapeutic agent for a muscle disease containing a myoregulin inhibitor as an active ingredient.

[2] The prophylactic or therapeutic agent according to [1], wherein the myoregulin inhibitor is a nucleic acid.

[3] The prophylactic or therapeutic agent according to [2], wherein the myoregulin inhibitor is an antisense oligonucleotide against myoregulin.

[4] The prophylactic or therapeutic agent according to any one of [1]-[3], wherein the muscle disease is selected from a group including muscular dystrophy, inclusion body myositis, amyotrophic lateral sclerosis, disused muscular atrophy, and sarcopenia.

[5] The prophylactic or therapeutic agent according to [4], wherein the muscular dystrophy is selected from a group including Duchenne muscular dystrophy, Becker muscular dystrophy, and sarcoglycanopathy.

[6] The prophylactic or therapeutic agent according to [4], wherein the muscular dystrophy is Duchenne muscular dystrophy.

[7] The prophylactic or therapeutic agent according to [4], wherein the muscular dystrophy is sarcoglycanopathy.

Effect of the Invention

According to the present invention, a symptom of a muscle disease such as muscular dystrophy can be ameliorated, and an effective medicament for prevention or treatment of the disease is provided.

MODE FOR CARRYING OUT THE INVENTION

Figure 1:
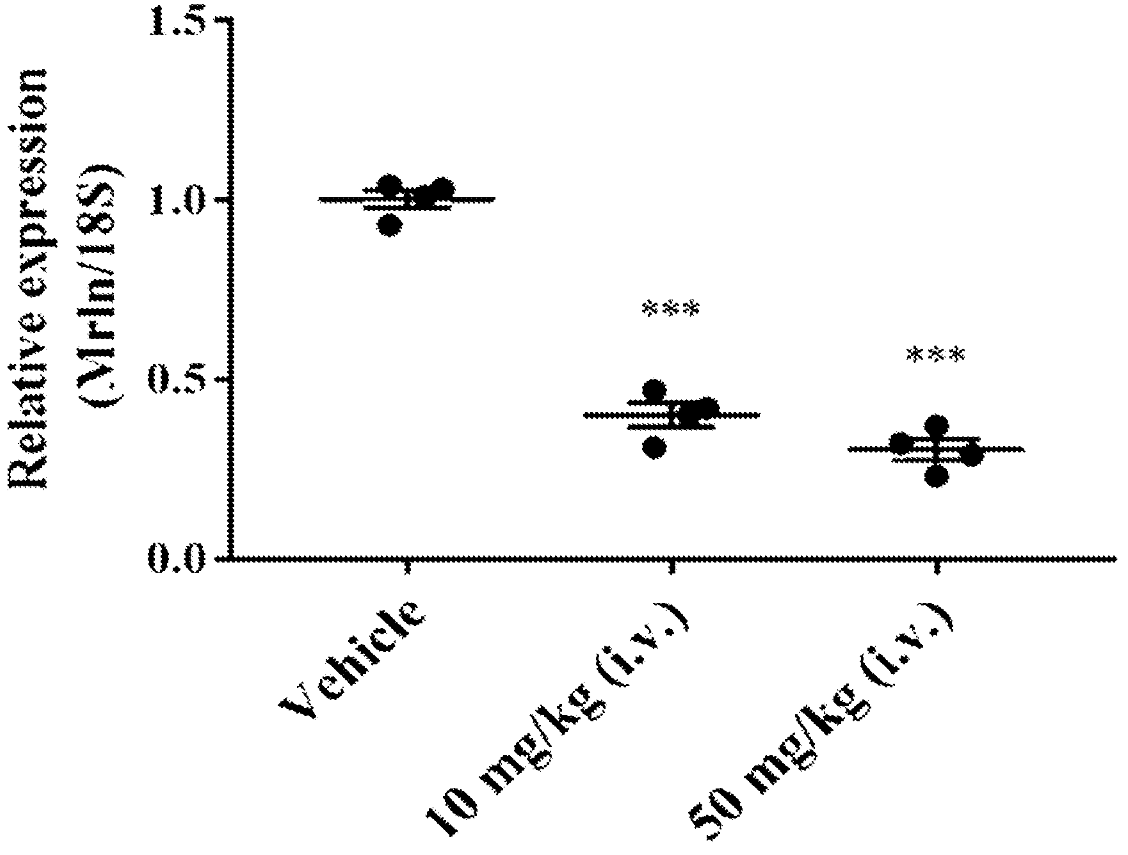
FIG. 1 A graph showing an MRLN expression inhibitory effect by an MRLN-specific antisense oligonucleotide.

It is to be understood that both the foregoing summary and the following detailed description are exemplary and explanatory only and are not restrictive of the present invention as claimed. Further, section headings used herein are for organizational purposes only and should not be construed as limiting the subject matter described.

(Definitions)

Unless a specific definition is given, the nomenclature used in connection with analytical chemistry, synthetic organic chemistry, and medical chemistry and pharmaceutical chemistry, and their procedures and techniques described herein are those that are commonly known in the art and are commonly used. Standard techniques can be used for chemical synthesis and chemical analysis as used herein. Where permitted, all patents, patent applications, published patent applications and other publications referred to throughout the disclosure of this specification, and GenBank accession numbers and relevant sequence information as well as other data available through databases such as the National Center for Biotechnology Information (NCBI), are incorporated by reference with respect to portions of the documents discussed herein, and in their entirety.

Further, this specification is filed together with a sequence listing in electronic format. However, the information of the sequence listing described in the electronic format is incorporated herein by reference in its entirety.

Unless otherwise indicated, the following terms have the following meanings.

"MRLN" means an oligonucleotide or protein that is known as myoregulin. MRLN includes, for example, various splicing variants transcribed from an MRLN gene, sequence variants such as single nucleotide substitutions (SNPs), and variant proteins translated from them.

A "nucleobase" means a heterocyclic moiety that can pair with a base of another nucleic acid.

A "nucleobase sequence" means an order of contiguous nucleobases forming an oligonucleotide.

A "nucleoside" means a molecule in which a sugar and a nucleobase are linked. In certain embodiments, a nucleoside is linked to a phosphate group.

A "nucleotide" means a molecule in which a phosphate group is linked to a sugar moiety of a nucleoside. In a naturally occurring nucleotide, a sugar moiety is a ribose or deoxyribose and is covalently linked by a phosphodiester bond via a phosphate group.

An "oligonucleotide" means a polymer of nucleosides in which nucleosides and internucleoside linkages are linked independently of each other.

"Complementary" means an ability with respect to pairing between nucleobases of a first nucleic acid and a second nucleic acid. In certain embodiments, adenine is complementary to thymidine or uracil. In certain embodiments, cytosine is complementary to guanine. In certain embodiments, 5-methylcytosine is complementary to guanine.

"Fully complementary (also called complementarity)" or "100% complementary (also called complementarity)" means that all nucleobases in a nucleobase sequence of a first nucleic acid have complementary nucleobases in a second nucleobase sequence of a second nucleic acid. In certain embodiments, a first nucleic acid is a modified oligonucleotide and a target nucleic acid is a second nucleic acid.

A "modified nucleoside" means a nucleoside having a modified sugar and/or a modified nucleobase. A "modified oligonucleotide" means an oligonucleotide that contains at least one of the modified nucleoside and/or the modified internucleoside linkage.

A "internucleoside linkage" refers to a chemical linkage between nucleosides, and a "modified internucleoside linkage" refers to a substitution or any change from a naturally occurring internucleoside linkage (that is, a 3-5' phosphodiester internucleoside linkage). For example, there is a phosphorothioate internucleoside linkage, but it is not limited to this. A "phosphorothioate internucleoside linkage" means an internucleoside linkage in which a phosphodiester linkage is modified by replacing one of non-crosslinked oxygen atoms with a sulfur atom.

A "modified nucleobase" refers to any nucleobase other than adenine, cytosine, guanine, thymidine or uracil. For example, there is a 5-methylcytosine, but it is not limited to this. "Unmodified nucleobases" means purine bases adenine (A) and guanine (G), and pyrimidine bases thymine (T), cytosine (C) and uracil (U).

A "sugar" or a "sugar moiety" means a natural sugar moiety or a modified sugar moiety. A "modified sugar" refers to a substitution or change from a natural sugar, and examples thereof include a substituted sugar moiety and a bicyclic sugar. Here, a "substituted sugar moiety" means a furanosyl other than a natural sugar of RNA or DNA, and a "bicyclic sugar" means a furanosyl ring modified by bridging of two different carbon atoms present on the same ring. A "bicyclic nucleic acid" refers to a nucleoside or nucleotide in which a furanose moiety of the nucleoside or nucleotide contains a "bicyclic sugar."

"siRNA" is an abbreviation for small interfering RNA, which is a double-stranded RNA consisting of about 20-30 base pairs used for gene silencing by RNA interference (RNAi). Further, shRNA is an abbreviation for short hairpin RNA, which is a hairpin type RNA sequence used for gene silencing by RNA interference.

"Antibodies" are polypeptides that specifically bind to particular antigens, and include polyclonal antibodies, monoclonal antibodies and antigen-binding fragments.

"Compounds" refer to all substances produced by chemical bonding of atoms such as C, H, O, N, S, and the like, and include low molecular weight compounds, peptides, sugars, polymer compounds, and the like.

"Administration" means providing an agent to an animal, and includes, but is not limited to, administration by a medical professional and self-administration.

An "effective amount" means an amount of the modified oligonucleotide of the present invention that is sufficient to achieve a desired physiological outcome in an individual in need of the drug. The effective amount can vary from individual to individual depending on health and physical conditions of an individual to be treated, a taxonomic group of the individual to be treated, a formulation of a composition, assessment of the individual's medical condition, and other relevant factors.

"Prevention" means delaying or preventing onset or development of a disease, disorder, unfavorable health condition, or one or more symptoms associated with the disease, disorder or undesired health condition for a period from minutes to indefinitely. Prevention also means reducing a risk of developing a disease, disorder, or undesirable health condition.

"Treatment" means alleviating or ameliorating or delaying progression of, or eliminating a disease, disorder, or unfavorable health condition, or one or more symptoms associated with the disease, disorder, or unfavorable health condition, or partially eliminating or eradicating one or more causes of the disease, disorder, or unfavorable health condition itself.

(Specific Embodiments)

Certain specific embodiments of the present invention described below provide, but are not limited to, a prophylactic or therapeutic agent for a muscle disease containing a myoregulin inhibitor as an active ingredient (hereinafter may be referred to as the agent of the present invention).

<Myoregulin>

Myoregulin (MRLN) is a micropeptide that is expressed in a skeletal muscle and regulates a sarcoplasmic reticulum calcium level, that is, suppresses calcium uptake in sarcoplasmic reticulum. MRLN may be any MRLN expressed in mammals such as humans and mice. However, human MRLN is preferred. An example of a nucleobase sequence of a mouse MRLN gene is a nucleobase sequence (SEQ ID NO: 1) registered in NCBI GenBank under an accession number NM_001304739.1, and an example of an amino acid sequence of a mouse MRLN protein encoded by this nucleobase sequence is SEQ ID NO: 2. An example of a nucleobase sequence of a human MRLN gene is a nucleobase sequence (SEQ ID NO: 3) registered in NCBI GenBank under an accession number NM_001304731.2, and an example of an amino acid sequence of a human MRLN protein encoded by this nucleobase sequence is SEQ ID NO: 4. When an mRNA nucleobase sequence is expressed, T is to be replaced with U in SEQ ID NOs: 1 and 3.

However, since a nucleobase sequence of an MRLN gene may have a difference in sequence depending on an individual, without being limited to the above sequences, as long as it encodes a micropeptide that regulates calcium in sarcoplasmic reticulum, specifically suppresses calcium uptake in sarcoplasmic reticulum, for example, a nucleobase sequence of a mouse MRLN may be a nucleobase sequence having an identity of 90%, 95%, or 98% or more with SEQ ID NO: 1, and a nucleobase sequence of a human MRLN gene may be a nucleobase sequence having an identity of 90%, 95%, or 98% or more with SEQ ID NO: 3. Further, as long as it has a function of regulating calcium in sarcoplasmic reticulum, specifically, suppressing calcium uptake in sarcoplasmic reticulum, an amino acid sequence of a mouse MRLN protein may be an amino acid sequence having an identity of 90%, 95%, or 98% or more with SEQ ID NO: 2, and an amino acid sequence of a human MRLN protein may be an amino acid sequence having an identity of 90%, 95%, or 98% or more with SEQ ID NO: 4.

<MRLN Inhibitor>

MRLN inhibitors include a substance that inhibits a function of MRLN and a substance that inhibits expression of MRLN.

An example of a function of MRLN is a function of suppressing calcium uptake into sarcoplasmic reticulum.

Therefore, an MRLN inhibitor is a substance that can increase calcium uptake into sarcoplasmic reticulum. An effect of an MRLN inhibitor on increasing calcium uptake into sarcoplasmic reticulum may be due to release of suppression of SERCA1 activity.

An increase in calcium uptake into sarcoplasmic reticulum can be measured using a system to be described later. As compared to a case where the agent of the present invention is not added or a negative control is added, the agent of the present invention preferably increases calcium uptake into sarcoplasmic reticulum by 1.1 or more times, preferably 1.2 or more times, and more preferably 1.5 or more times.

The agent of the present invention may be an agent that directly acts on MRLN to inhibit the above function, or an agent that indirectly acts on MRLN to inhibit the above function.

On the other hand, WRLN expression inhibition means reducing an amount of at least one of pre-mRNA, mRNA and a protein of MRLN.

MRLN expression inhibition can be evaluated using an expression measurement system to be described below. As compared to a case where the agent of the present invention is not added or a negative control is added, the agent of the present invention preferably reduces an amount of pre-mRNA, mRNA and/or a protein of MRLN to 70% or less, preferably 50% or less, and preferably 30% or less.

A type of an MRLN inhibitor is not particularly limited as long as the MRLN inhibitor can inhibit a function and/or expression of MRLN. However, examples thereof include a nucleic acid (oligonucleotide), an antibody, a compound, and the like.

Specifically, examples of a nucleic acid, which is an MRLN inhibitor, include an antisense oligonucleotide against MRLN, siRNA, shRNA, or a vector expressing these. However, an antisense oligonucleotide against MRLN is preferably used.

An antisense oligonucleotide against MRLN is preferably an antisense oligonucleotide consisting of 10-50 bases, preferably 15-30 bases and containing a nucleobase sequence (hereinafter referred to as an "MRLN complementary nucleobase sequence") of at least 8 contiguous bases that is 100% complementary to an equal length portion of a nucleobase sequence of MRLN (for example, SEQ ID NOs: 1 and 3 or a nucleobase sequence having an identity of 90%, 95%, or 98% or more with SEQ ID NOs: 1 and 3). Here, an equal length portion means a portion having complementarity between a nucleobase sequence of an antisense oligonucleotide and a nucleobase sequence of MRLN.

An antisense oligonucleotide against MRLN may have a nucleobase sequence of 10-50 bases in full length including the above MRLN-complementary nucleobase sequence, and may have one or more mismatched nucleobases or additional bases in a portion other than the MRLN complementary nucleobase sequence, and may have, in full length, a complementarity of 85% or more, 90% or more, and preferably 95% or more to an equal length portion of a nucleobase sequence of MRLN (for example, SEQ ID NOs: 1 and 3).

Percent complementarity of an antisense oligonucleotide, which is an MRLN inhibitor, with respect to a nucleobase sequence of MRLN can be determined conventionally, for example, using the BLAST program (basic local alignment search tools), the PowerBLAST program (Altschul et al., J. Mol. Biol., 1990, 215, 403 410; Zhang and Madden, Genome Res., 1997, 7, 649 656), or default settings of the Genetyx software (GENETYX CORPORATION), which are known in the art. Percent homology, sequence identity or complementarity, can be determined, for example, by the Gap program (Wisconsin Sequence Analysis Package, Version 8 for Unix, Genetics Computer Group, University Research Park, Madison Wis.), using default settings using the algorithm of Smith and Waterman (Adv. Appl. Math., 1981, 2, 482 489), or using default settings of the Genetyx software (GENETYX CORPORATION).

An antisense oligonucleotide against MRLN can be a modified oligonucleotide. A modified oligonucleotide may contain a modified base such as a 5-methylcytosine, or at least one nucleoside forming an oligonucleotide may contain a modified sugar. Further, an internucleoside linkage may be modified.

Here, a modified sugar refers to a sugar in which a sugar moiety is modified, and a modified oligonucleotide containing one or more such modified sugars has advantageous characteristics such as enhanced nuclease stability and increased binding affinity. Preferably, at least one of the modified sugars has a bicyclic sugar or a substituted sugar moiety.

Examples of nucleosides having modified sugars include nucleosides containing 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituents. A substituent at a 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$ and O—$CH_2$—C(═O)—$N(R_l)$—$(CH_2)_2$—$N(R_m)(R_n)$ (wherein $R_l$, $R_m$ and $R_n$ are each independently H or substituted or unsubstituted $C_1$-$C_{10}$ alkyl).

Examples of nucleosides having a bicyclic sugar include nucleosides that contain a bridge between 4' and 2' ribosyl ring atoms. In certain embodiments, an oligonucleotide provided herein includes a nucleoside having one or more bicyclic sugars, in which a bridge includes one of the following formulas: 4'-$(CH_2)$—O-2' (LNA); 4'-$(CH_2)$—S-2'; 4'-$(CH_2)_2$—O-2' (ENA); 4'-$CH(CH_3)$—O-2' and 4'-CH $(CH_2OCH_3)$—O-2' (and analogs thereof, see U.S. Pat. No. 7,399,845); 4'-$C(CH_3)(CH_3)$—O-2' (and analogs thereof, see WO 2009/006478); 4'-$CH_2$—$N(OCH_3)$-2' (and analogs thereof; see WO 2008/150729); 4'-$CH_2$—O—$N(CH_3)$-2' (see US 2004-0171570); 4'-$CH_2$—N(R)—O-2' (wherein R is H, $C_1$-$C_{12}$ alkyl or a protecting group) (see U.S. Pat. No. 7,427,672); 4'-$CH_2$—$C(H)(CH_3)$-2' (see Chattopadhyaya et al., J. Org. Chem., 2009, 74, 118-134); and 4'-$CH_2$—C (═$CH_2$)-2' (and analogues thereof; see WO 2008/154401).

In certain embodiments, a nucleoside containing a bicyclic sugar can be a nucleoside containing a sugar moiety of a bridging artificial nucleic acid ALNA disclosed in WO 2020/100826, and can be, for example, a nucleoside containing a sugar moiety of ALNA [Ms] represented by the following general formula (I):

[Chemical Formula 1]

(I)

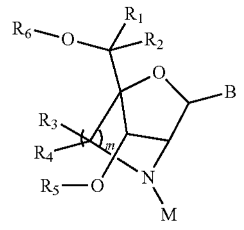

[wherein

B is a nucleobase;

$R_1$, $R_2$, $R_3$, and $R_4$ are each independently a hydrogen atom or a $C_{1-6}$ alkyl group that may be substituted with one or more substituents;

$R_5$ and $R_6$ are each independently a hydrogen atom, a protecting group of a hydroxyl group, a phosphate group that may be substituted, a phosphorus moiety, a covalent attachment to a support, or the like;

m is 1 or 2; and

M is a sulfonyl group substituted with a methyl group that may be substituted with one or more substituents. A typical specific example of ALNA [Ms] is a nucleoside in which M is a sulfonyl group substituted with an unsubstituted methyl group.

In certain embodiments, an antisense oligonucleotide as an MRLN inhibitor has a nucleobase sequence in which at least one nucleobase is a cytosine. In certain embodiments, at least one cytosine is a 5-methylcytosine of a modified nucleobase.

A naturally occurring internucleoside linkage of RNA and DNA is a 3'-5' phosphodiester linkage.

An oligonucleotide having one or more modified, that is, non-naturally occurring, internucleoside linkages is often preferred over an oligonucleotide having a naturally occurring internucleoside linkage because of properties such as, for example, enhanced cellular uptake, enhanced affinity for a target nucleic acid, and increased stability in the presence of nucleases.

An oligonucleotide having modified internucleoside linkages include internucleoside linkages that retain a phosphorus atom and internucleoside linkages that do not have a phosphorus atom. Representative phosphorus-containing internucleoside linkages include, but are not limited to, one of more of phosphodiesters, phosphotriesters, methylphosphonates, phosphoramidate, and phosphorothioates. Methods for preparing phosphorous-containing and non-phosphorous-containing linkages are commonly known.

In certain embodiments, internucleoside linkages of an antisense oligonucleotide as an MRLN inhibitor are all phosphorothioate internucleoside linkages.

An antisense oligonucleotide as MRLN inhibitor can be synthesized using a conventional method, for example, can be easily synthesized using a commercially available nucleic acid synthesizer. Further, a sugar-modified ALNA [Ms] of a nucleoside, which may be contained in an antisense oligonucleotide, can be synthesized using a method disclosed in WO 2020/100826.

siRNA against MRLN is a double-stranded oligo RNA having a sequence complementary to a partial sequence (usually 20 bases or more, preferably 21 bases or more, and usually 30 bases or less, preferably 27 bases or less, more preferably 23 bases or less) of mRNA of MRLN, and is not particularly limited as long as it can inhibit MRLN expression by specifically recognizing and cleaving this transcript. Based on a nucleobase sequence of a mouse MRLN gene described in SEQ ID NO: 1 or a nucleobase sequence of a human MRLN gene described in SEQ ID NO: 3, a person skilled in the art can determine sequences of sense and antisense strands of siRNAs that can be used for inhibiting MRLN expression in a human or a mouse. siRNA may be synthesized using a commonly known method, and, for example, can be synthesized by synthesizing each of a sense strand and an antisense strand by DNA/RNA chemical synthesis or enzymatic synthesis and annealing them.

As an expression vector, any expression vector used in the art can be used, and examples thereof include *Escherichia coli*-derived plasmids (for example, pBR322, pBR325, pUC12, pUC13), *Bacillus subtilis*-derived plasmids (for example, pUB110, pTP5, pC194), yeast-derived plasmids (for example, pSH19, pSH15), bacteriophage such as phage lambda, animal viruses such as retroviruses, vaccinia viruses, and baculoviruses, and the like, and further include pA1-11, pXT1, pRc/CMV, pRc/RSV, pcDNAI/Neo, and the like.

The antibody against MRLN is an antibody that specifically binds to MRLN, and an antagonist antibody that inhibits a function of MRLN by binding.

As used herein, "antibodies" include: natural antibodies such as polyclonal antibodies and monoclonal antibodies; chimeric antibodies that can be produced using a genetic recombination technology; humanized antibodies or single chain antibodies; human antibodies that can be produced using human antibody-producing transgenic animals and the like; antibodies produced by phage display; and binding fragments of these.

A binding fragment means a partial region of an antibody described above, and specific examples thereof include F(ab')2, Fab', Fab, Fv (variable fragment of antibody), sFv, dsFv (disulphide stabilized Fv), dAb (single domain antibody) and the like (Exp. Opin. Ther. Patents, Vol. 6, No. 5, P. 441-456, 1996).

An antibody class is not particularly limited and also includes antibodies having any isotype such as IgG, IgM, IgA, IgD or IgE. IgG or IgM is preferred, and IgG is more preferred considering ease of purification and the like.

A polyclonal antibody can be produced, for example, as follows. That is, immune sensitization is performed by injecting immunogen subcutaneously, intramuscularly, intravenously, in the footpad or intraperitoneally in animals, such as mice, rats, hamsters, guinea pigs, goats, horses or rabbits, one to several times. Usually, immunization is performed 1 to 5 times about every 1 to 14 days after the initial immunization, and serum is obtained from an immune-sensitized animal about 1 to 5 days after the final immunization. It is also possible that the serum is directly used as a polyclonal antibody, but preferably, the serum is isolated and/or purified by affinity column chromatography using ultrafiltration, ammonium sulfate fractionation, euglobulin precipitation, a caproic acid method, a caprylic acid method, ion-exchange chromatography (DEAE or DE52, or the like), anti-immunoglobulin column or protein A/G column, column with cross-linked immunogen, and the like.

A monoclonal antibody can be produced, for example, as follows. That is, it is produced by preparing a hybridoma from antibody-producing cells, which are obtained from an immune-sensitized animal such as a mouse, rat or hamster that has been administered with an immunogen, and myeloma cells having no autoantibody-producing ability, cloning the hybridoma, and selecting a clone that produces a monoclonal antibody exhibiting specific affinity for an immunogen used for immunization of a mammal.

Preparation of a hybridoma (fused cell) secreting a monoclonal antibody can be performed according to a method of Koehler and Milstein et al. (Nature, Vol. 256, P. 495-497, 1975) and methods modified based thereon. As myeloma cells used for cell fusion, for example, mouse-derived myeloma p3/X63-AG8.653 (653; ATCC No. CRL1580), p3/NSI/1-Ag4-1 (NS-1), p3/X63-Ag8.U1 (p3U1), SP2/0-Agl4 (Sp2/0, Sp2), PAI, FO or BW5147, rat-derived myeloma 210RCY3-Ag.2.3., and human-derived myeloma U-266AR1, GM1500-6TG-A1-2, UC729-6, CEM-AGR, D1R11 or CEM-T15 can be used.

Screening for a hybridoma clone that produces a monoclonal antibody can be performed by culturing a hybridoma, for example, in a microtiter plate, and measuring reactivity of a culture supernatant of a well in which proliferation is observed with respect to an immunogen used in the above-described immune sensitization using, for example, an enzyme immunoassay method such as ELISA. Similar to the polyclonal antibody described above, the monoclonal antibody is preferably isolated and/or purified.

A chimeric antibody can be produced, for example, by referring to "Experimental Medicine (Extra Issue), Vol. 6, No. 10, 1988," Japanese Patent Publication No. H3-73280, and the like, a humanized antibody can be produced, for example, by referring to Japanese Translation of PCT International Application Publication No. H4-506458, Japanese Patent Application Laid-Open Publication No. S62-296890, and the like, and a human antibody can be produced, for example, by referring to "Nature Genetics, Vol. 15, P. 146-156, 1997," "Nature Genetics, Vol. 7, P. 13-21, 1994," Japanese Translation of PCT International Application Publication No. H4-504365, International Publication No. WO 94/25585, "Nature, Vol. 368, P. 856-859, 1994," Japanese Translation of PCT International Application Publication No. H6-500233, and the like.

Antibody production by phage display allows an antibody such as Fab or the like to be easily obtained from a phage library created for antibody screening by collecting and concentrating a phage having affinity to an antigen, for example, by biopanning. For antibody production by phage display, see "Nature, Vol. 348, P. 552-554, 1990," "Phage display a laboratory manual" in cold spring harbor laboratory press, 2001, "Antibody Engineering—a Practical Approach, IRL Press, Oxford, 1996."

F(ab)2 and Fab' can each be produced by treating immunoglobulin with pepsin or papain, which are proteolytic enzymes. Fab can be produced by screening a Fab-expressing phage library in the same manner as in the antibody production method by phage display described above.

An MRLN inhibitor, which is an active ingredient of the agent of the present invention, may be a compound that inhibits a function or expression of MRLN. The compound is not limited in structure as long as the compound can inhibit a function or expression of MRLN, and may be any of a low-molecular-weight compound, a peptide, a sugar, a polymer compound, and the like. The compound can be obtained by screening.

<Method for Evaluating or Screening MRLN Inhibitor>

As a method for evaluating or screening (selecting) an MRLN inhibitor, any method can be used as long as it is a method that allows inhibition of expression or inhibition of a function of MRLN in cells to be verified. However, specifically, for example, the following in vitro and in vivo verification methods are used.

In evaluating or screening an MRLN inhibitor, when MRLN expression inhibition is used as an indicator, there is a method in which an inhibitor or a candidate substance thereof is added to MRLN-expressing cells or tissue, and an MRLN mRNA or protein expression level is measured and is compared with that when the inhibitor or the candidate substance is not added or when a negative control is added.

Examples of MRLN-expressing cells include myoblast cells and myotube cells, and an example of cultured muscle cells is C2C12 cells used in Examples. Cells into which an MRLN gene has been exogenously introduced may be used.

Further, an MRLN inhibitor may be administered to a non-human animal and an MRLN expression level in a muscle tissue of the animal may be measured, or an MRLN inhibitor may be administered to an isolated muscle tissue, and an MRLN expression level in the muscle tissue may be measured.

By measuring an MRLN expression level in such an in vitro or in vivo MRLN expression level measurement system, an MRLN inhibitor can be screened or evaluated.

A method for bring an MRLN inhibitor into contact with MRLN-expressing cells is also not particularly limited. However, when an MRLN inhibitor is a nucleic acid, a method generally used for introducing a nucleic acid into cells, such as a lipofection method, an electroporation, method, or a gymnosis method, can be used.

An intracellular mRNA expression level of MRLN can be measured using various methods known in the art. Specific examples include Northern blot analysis, competitive polymerase chain reaction (PCR) or quantitative real-time PCR, and the like. When isolating mRNA, a method commonly known in the art is used, for example, SuperPrep Cell Lysis & RT Kit for qPCR (Toyobo), RNeasy Fibrous Tissue Mini Kit (Qiagen), and the like can be used according to manufacturers' recommended protocols. In this way, an MRLN expression level can be measured.

A protein expression level in MRLN cells can be assayed using various methods known in the art. Specific examples thereof include immunoprecipitation, Western blot analysis (*immunoblot method), enzyme-linked immunosorbent assay (ELISA), quantitative protein assay, protein activity assay (for example, caspase activity assay), immunohistochemical method, immunocytochemical method or fluorescence activated cell sorting (FACS), and the like.

In evaluating or screening of an MRLN inhibitor, when MRLN function inhibition is used as an indicator to screen or evaluate an MRLN inhibitor, for example, calcium uptake into sarcoplasmic reticulum and calcium release from sarcoplasmic reticulum can be used as indicators. As an example, in a system in which ryanodine receptor agonist is added to muscle cells to perform stimulation and an amount of calcium released from sarcoplasmic reticulum is measured, by causing an MRLN inhibitor or a candidate substance thereof to be present and examining an effect thereof, the MRLN inhibitor can be screened or evaluated. In a muscle disease, calcium leakage from sarcoplasmic reticulum occurs, the calcium level in sarcoplasmic reticulum decreases, and a calcium release amount from sarcoplasmic reticulum due to ryanodine receptor agonist stimulation decreases. However, due to the presence of an MRLN inhibitor, the calcium level in sarcoplasmic reticulum is restored and the amount of calcium released from sarcoplasmic reticulum is increased (restored). Therefore, an MRLN inhibitor can be screened or evaluated using the increase in (restoration of) the calcium release amount as an indicator.

An MRLN inhibitor can also be evaluated or screened using a muscle disease model animal. As a muscle disease model animal, for example, a dystrophin-deficient mouse or a sarcoglycan-deficient mouse can be used.

For example, in these deficient mice, a creatine kinase level in blood is increased as compared to normal mice. However, by administering an MRLN inhibitor, the creatine kinase level in blood is decreased. Therefore, an MRLN inhibitor can be evaluated or screened using this reduction in creatine kinase level in blood as an indicator.

Further, an MRLN inhibitor can also be evaluated or screened using amelioration of a pathological condition such as muscle fiber collapse or cell death in a muscle disease model animal as an indicator.

An MRLN inhibitor obtained using a selection method of the present invention suppresses development or progression of a muscle disease, and thus, can be used as a prophylactic and/or therapeutic agent for a muscle disease. That is, the present invention provides a screening method for a prophylactic and/or therapeutic agent for a muscle disease, the method comprising a process of selecting an MRLN inhibitor using the above-described method. The screening method preferably includes a process of evaluating both an ability of a candidate substance to inhibit MRLN expression and an ability of the candidate substance to inhibit a function of MRLN such as calcium release from sarcoplasmic reticulum.

<Treatment of a Muscle Disease Using an MRLN Inhibitor>

In the present invention, a muscle disease can be treated or prevented using an MRLN inhibitor.

Examples of muscle diseases include, but are not limited to, muscular dystrophy, inclusion body myositis, amyotrophic lateral sclerosis, disuse muscle atrophy, and sarcopenia. Among these, muscular dystrophy is preferred. A typical example of muscular dystrophy is muscular dystrophy having a mutation or a defect in a component of a dystrophin-glycoprotein complex (DGC), and examples thereof include Duchenne muscular dystrophy, Becker muscular dystrophy, and limb muscular dystrophy (such as sarcoglycanopathy). Sarcoglycanopathies include LGMD2C, LGMD2D, LGMD2E, and LGMD2F.

A muscle disease is preferably a disease with abnormal calcium influx in cytoplasm of muscle cells.

An MRLN inhibitor has a function of increasing sarcoplasmic reticulum calcium uptake by inhibiting a function or expression of MRLN, thereby reducing a calcium level in cytoplasm.

Therefore, it is effective for treating or preventing a muscle disease such as that described above with abnormal calcium influx into cytoplasm.

In particular, for a pathological condition of muscular dystrophy, two mechanisms have been suggested: (1) due to DGC deficiency, membrane permeability increases, and thereby, a calcium level in cytoplasm increases and cell death occurs; and (2) due to DGC deficiency, nNOS (neuronal nitric oxide synthase) deceases and, in cytoplasm, iNOS (inducible nitric oxide synthase) increases, and a ryanodine receptor is nitrosylated, and a calcium level in sarcoplasmic reticulum decreases and muscle contraction is reduced.

An MRLN inhibitor suppresses muscle cell death and maintains or restores muscle contractility by decreasing calcium level in cytoplasm and increasing calcium uptake in sarcoplasmic reticulum, and thereby, achieves a therapeutic effect and/or a prophylactic effect with respect to a muscle disease.

That is, the agent of the present invention can be an agent that suppresses muscle cell death or an agent that maintains or restores muscle contractility.

Therefore, the present invention provides: a therapeutic or prophylactic agent for a muscle disease or a pharmaceutical composition for treating or preventing a muscle disease, containing an MRLN inhibitor as an active ingredient; a method for treating or preventing a muscle disease, comprising a process of administering an effective amount of an MRLN inhibitor to a subject in need of treatment or prevention of a muscle disease; an MRLN inhibitor for treating or preventing a muscle disease; and use of an MRLN inhibitor in manufacture of a medicament for treating or preventing of a muscle disease.

The agent of the present invention can be prepared with an MRLN inhibitor as it is or by blending it with a pharmacologically acceptable carrier. As pharmacologically acceptable carriers, various organic or inorganic carrier substances that are commonly used as pharmaceutical materials are used, and are blended as: excipients, lubricants, binders, disintegrants in solid preparations; and solvents, solubilizers, suspending agents, tonicity agents, buffers, soothing agents, and the like in liquid preparations. Further, when necessary, formulation additives such as preservatives, antioxidants, coloring agents and sweetening agents can also be used.

Further, when the MRLN inhibitor is a nucleic acid, the agent of the present invention can contain a nucleic acid introduction reagent. As the nucleic acid introduction reagent, liposome, lipofectin, lipofectamine, DOGS (transfectum), DOPE, DOTAP, DDAB, DHDEAB, HDEAB, polybrene, or cationic lipids such as poly (ethyleneimine) (PEI), or the like can be used.

The agent of the present invention can be administered orally or parenterally to a subject in need of treatment or prevention of a muscle disease. Examples of parenteral administration include subcutaneous administration, intravenous administration, intramuscular administration, intraarterial administration, intraperitoneal administration, and the like. Administration may be continuous or long-term, or may be short-term or intermittent.

Examples of dosage forms for oral administration include tablets (including sugar-coated tablets and film-coated tablets), pills, granules, powders, capsules (including soft capsules and microcapsules), syrups, emulsions, suspensions, and the like.

On the other hand, examples of dosage forms for parenteral administration include injections, impregnating agents, infusions, suppositories, and the like. Further, it is also effective to combine with a suitable base (for example, a butyric acid polymer, a glycolic acid polymer, a butyric acid-glycolic acid copolymer, a mixture of a butyric acid polymer and a glycolic acid polymer, polyglycerol fatty acid ester, or the like) to prepare a sustained-release preparation.

As a method for formulating an MRLN inhibitor into a dosage form described above, a commonly known production method generally used in the art can be applied. Further, when producing the dosage forms described above, when necessary, carriers such as excipients, binders, disintegrants, lubricants, and the like that are commonly used in the pharmaceutical field when preparing the dosage forms, and various formulation additives such as sweeteners, surfactants, suspending agents, emulsifiers, and the like, can be appropriately added in appropriate amounts to produce the dosage forms.

For example, as an agent for parenteral administration, preferably, an injection is used. Injections include intravenous injections, subcutaneous injections, intradermal injections, intramuscular injections, drip injections, and the like. Such an injection is prepared according to a commonly known method, for example, by dissolving, suspending or emulsifying an MRLN inhibitor such as the antisense oligonucleotides described above in a sterile aqueous or oily solution usually used for injections. As an aqueous solution for injection, for example, phosphate buffered saline, physiological saline, an isotonic solution containing glucose or other adjuvants, and the like are used, and may be used in combination with a suitable solubilizing agent, for example, alcohol (for example, ethanol), polyalcohol (for example, propylene glycol, polyethylene glycol), nonionic surfactant [for example, polysolvate 80, HCO-50 (polyoxyethylene (50 mol) adduct of hydrogenated castor oil)], and the like. Further, a buffering agent, a pH adjusting agent, an isotonizing agent, a soothing agent, a preservative, a stabilizer, and the like can be contained. Such compositions are produced using commonly known methods.

A ratio of an active ingredient, that is, an MRLN inhibitor, contained in the agent of the present invention can be appropriately set in a range that allows a desired effect to be achieved, but is usually 0.01-100% by weight, preferably 0.1-99.9% by weight, and more preferably 0.5-99.5% by weight.

The agent of the present invention containing an MRLN inhibitor as an active ingredient is stable and has low toxicity and can be safely used. A daily dose thereof is not generally defined according to a type of active ingredient, a body weight and age of a subject, a symptom, and the like, but can be selected in a range of 0.1 ng-1000 mg per 1 kg body weight per dose, and preferably in a range of 1 ng-100 mg/kg/week.

An administration frequency of the agent of the present invention is not particularly limited, but is usually about 1-10 times per month. Further, an administration period may be short-term administration of several days to about one week, long-term administration of several weeks to several months, or several years to several decades. When a symptom of a disease recurs after a considerable interval, the agent of the present invention can be administered again.

A subject to which the agent of the present invention is to be administered is a subject who requires treatment or prevention of a muscle disease. However, examples of a subject to be administered include mammals such as mice, rats, hamsters, guinea pigs, rabbits, cats, dogs, cows, horses, sheep, monkeys and humans, and primates are preferred, and humans are particularly preferred.

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references described in this application is incorporated herein by reference in its entirety.

EXAMPLES

The present invention is more specifically described with reference to examples below. However, the present invention is not limited to these examples.

Example 1

Preparation of Modified Antisense Oligonucleotide

A modified antisense oligonucleotide was synthesized and purified by Nippon Gene Co., Ltd./Nippon Gene Materials Co., Ltd. according to a general solid-phase synthesis method for an oligonucleic acid. Compound identification was performed using a high-performance liquid chromatography-mass spectrometer.

A synthesized MRLN antisense oligonucleotide is a modified antisense oligonucleotide consisting of 16 bases complementary to positions 409-424 of a mouse MRLN nucleobase sequence (SEQ ID NO: 1).

Example 2

In Vitro MRLN Knockdown Activity Test (Gymnosis Method)

C2C12 cells were seeded in a 384 plate and cultured in a $CO_2$ incubator. After 3 hours, the MRLN antisense oligonucleotide synthesized in Example 1 was added and the cells were cultured in a $CO_2$ incubator. After about 72 hours, an MRLN antisense oligonucleotide-containing medium was removed from the cells and washing with phosphate-buffered saline (PBS) was performed. After that, using SuperPrep Cell Lysis & RT Kit for qPCR (Toyobo), a cell lysate containing RNA was prepared, and reverse transcription from the lysate was performed, and template cDNA was synthesized. Using this cDNA, real-time PCR was performed and an MRLN mRNA expression level was quantified. A processing concentration of the MRLN antisense oligonucleotide was 1000 nM at a highest concentration, and one diluted at a concentration of a common ratio of 3 to 4 was used, and $IC_{50}$ was calculated as MRLN knockdown activity. The test was performed three times, and an average value of $IC_{50}$ was 119.9 nM. In this way, it is shown that the MRLN antisense oligonucleotide inhibits MRLN expression.

Example 3

In Vivo MRLN Knockdown Activity Test

The MRLN antisense oligonucleotide synthesized in Example 1 was prepared with physiological saline at 10 and 50 mg/(5 mL)/kg, and was administered to a 7-week-old C57BL/10ScSn-Dmdmdx/J (mdx) mouse (male, Jackson Laboratory) via the tail vein. The mdx mouse is a mouse that is most used as a DMD model mouse. After about 72 hours, whole blood was collected from the abdominal vena cava under isoflurane (Pfizer) anesthesia, and the mouse was lethally killed. After lethality, the tibialis anterior muscle was collected and immersed in RNAlater Soln (invitrogen). An RLT buffer of RNeasy Fibrous Tissue Mini Kit (Qiagen) was added to the tissue, and the tissue was crushed using a multi-bead shocker, and RNA was purified according to the protocol described in the kit. 200 ng of RNA was reverse transcribed and quantitative PCR was performed using obtained cDNA. Knockdown activity of the MRLN antisense oligonucleotide was expressed as a quantitative ratio of MRLN to 18S rRNA relative to a vehicle group. The results are shown in FIG. 1. It is shown that the MRLN antisense oligonucleotide inhibits MRLN expression in muscle.

Example 4

MRLN Antisense Oligonucleotide Administration Test with Respect to Muscular Dystrophy Model Mouse The MRLN antisense oligonucleotide synthesized in Example 1 was prepared with physiological saline at an appropriate concentration, and was administered to a mdx mouse, a sarcoglycan β (Sgcb) knockout mouse, a sarcoglycan alpha (Sgca) knockout mouse, a sarcoglycan gamma (Sgcg) knockout mouse, a sarcoglycan delta (Sgcd) knockout mouse, or a dystrophin/utrophin double knockout mouse via the tail vein. A group to be administered an appropriate number of times was set, and a few days to one week after the final administration, whole blood was collected from the abdominal vena cava under anesthesia, and the mouse was lethally killed. Creatine kinase (CK) is measured using a collected plasma or serum. After lethality, a portion of a skeletal muscle tissue is collected for pathological analysis and is fixed by immersion in a 10% neutral buffered formalin solution. A portion of the skeletal muscle tissue is collected for genetic analysis and is immersed in RNAlater Soln (Invitrogen). RNA extraction for genetic analysis is performed by adding an RLT buffer of RNeasy Fibrous Tissue Mini Kit (Qiagen) to the tissue and then crushing it using a multi-bead shocker, according to the protocol described in the kit. 200 ng of RNA is reverse transcribed and quantitative PCR is performed using obtained cDNA. For the skeletal muscle tissue after the formalin fixation, tissue specimens are prepared by preparing paraffin sections and performing immunostaining with an IgG antibody (Anti-IgG (H+L) Mouse, Goat-Poly Biotin, Vector Laboratories). Each of the tissue specimens is photographed using Aperio AT2 (Leica Biosystems). Using this digital image, a positive area of IgG immunostaining is quantitatively analyzed using the Area Quantification Module of the image analysis software "HALO," and a ratio (%) of the positive area to a total area is calculated. A positive area of IgG immunostaining is an indicator of necrotic fibrosis of cells. By administering an MRLN antisense oligonucleotide, suppression of MRLN gene expression, reduction of CK in plasma or serum, and improvement in skeletal muscle pathological image are confirmed.

Figure 2:
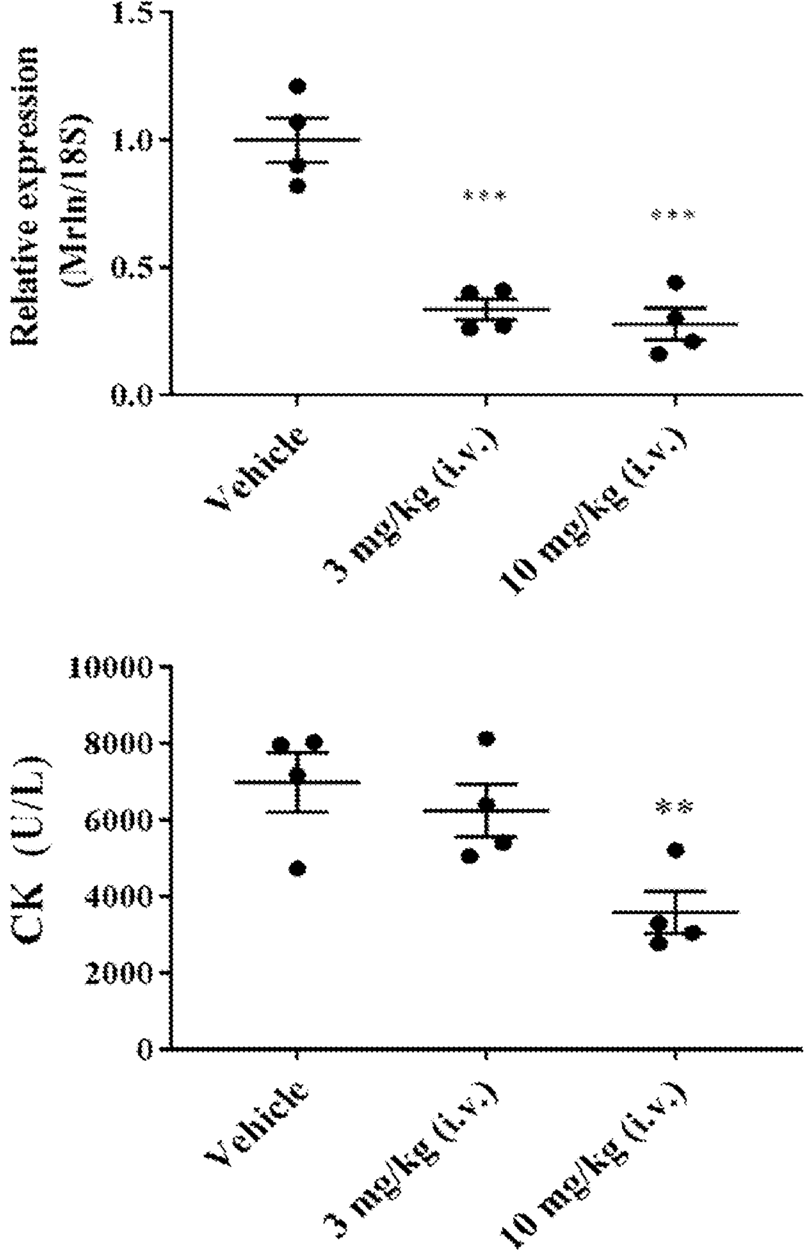
FIG. 2 Graphs showing an MRLN expression level ratio and a creatine kinase (CK) value when an MRLN-specific antisense oligonucleotide is administered to mdx mice.
Figure 3:
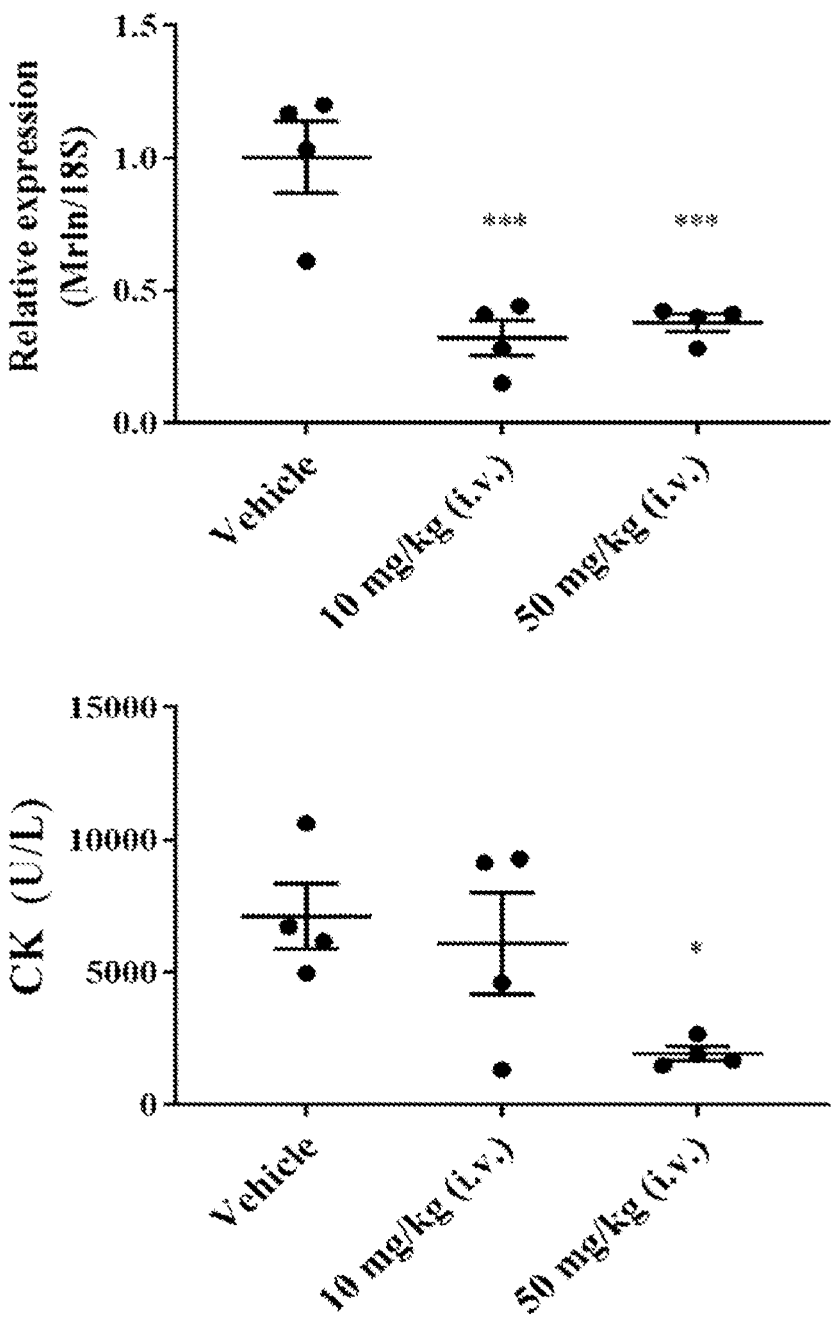
FIG. 3 Graphs showing an MRLN expression level ratio and a CK value when an MRLN-specific antisense oligonucleotide is administered to Sgcb knockout mice.

Specifically, an expression level ratio of MRLN and a value of CK were analyzed as follows. The MRLN antisense oligonucleotide synthesized in Example 1 was prepared with physiological saline at 3 and 10 mg/(5 mL)/kg, and was administered to a 8-week-old C57BL/10ScSn-Dmdmdx/J (mdx) mouse (male, Jackson Laboratory) via the tail vein. Administration was performed once a week for two times, and one week after the final administration, whole blood was collected from the abdominal vena cava under isoflurane (Pfizer Inc.) anesthesia, and the mouse was lethally killed. Further, the above MRLN antisense oligonucleotide were prepared with physiological saline at 10 and 50 mg/(5 mL)/kg, and was administered to a 15-week-old sarcoglycan β (Sgcb) knockout mouse via the tail vein. The Sgcb knockout mouse is a model mouse of sarcoglycanopathy and was generated by deleting Exon2 of a Sgcb gene. Three days after the administration, whole blood was collected from the abdominal vena cava under sevoflurane (Maruishi Pharmaceutical Co., Ltd.) anesthesia, and the mouse was lethally killed. After lethality, the tibialis anterior muscle was collected and immersed in RNAlater Soln (invitrogen). An RLT buffer of RNeasy Fibrous Tissue Mini Kit (Qiagen) was added to the tissue, and the tissue was crushed using a multi-bead shocker, and RNA was purified according to the protocol described in the kit. 200 ng of RNA was reverse transcribed and quantitative PCR was performed using obtained cDNA. Creatine kinase (CK) was measured using a collected plasma. FIG. 2 shows the results of the mdx mice, and FIG. 3 shows the results of the Sgcb knockout mice. The MRLN antisense oligonucleotides inhibited MRLN expression and decreased CK in both the model mice.

Example 5

Intracellular Calcium Measurement Test Using Muscular Dystrophy Patient-Derived Cells DMD and sarcoglycanopathy (LGMD2E) patient-derived myoblasts are seeded in a 96-well plate or 384-well plate and cultured in a $CO_2$ incubator. During a culture period, differentiation induction is performed in a state in which the cells are semi-confluent. After the cells differentiated into myotubes, the MRLN antisense oligonucleotide, or the MRLN antisense oligonucleotide mixed with siRNA or a transfection reagent (Lipofectamine RNAi Reagent, or the like), or siRNA, is treated, and the cells were further cultured in a $CO_2$ incubator. The MRLN antisense oligonucleotide or siRNA to be used is an antisense oligonucleotide or siRNA complementary to a portion of a human MRLN nucleobase sequence (SEQ ID NO: 3). A few days after the MRLN antisense oligonucleotide or siRNA is treated, a medium containing the MRLN antisense oligonucleotide or siRNA is removed from the cells, a loading dye containing a calcium dye is added, and incubation at room temperature is performed. One hour later, intracellular calcium measurement by FDSS is performed. When the calcium measurement is performed, in order to stimulate the cells, a ryanodine receptor agonist or the like is used. An increase in sarcoplasmic reticulum calcium in patient-derived cells due to the MRLN antisense oligonucleotide or siRNA treatment is confirmed.

Specifically, the intracellular calcium measurement was performed as follows.

Figure 4:
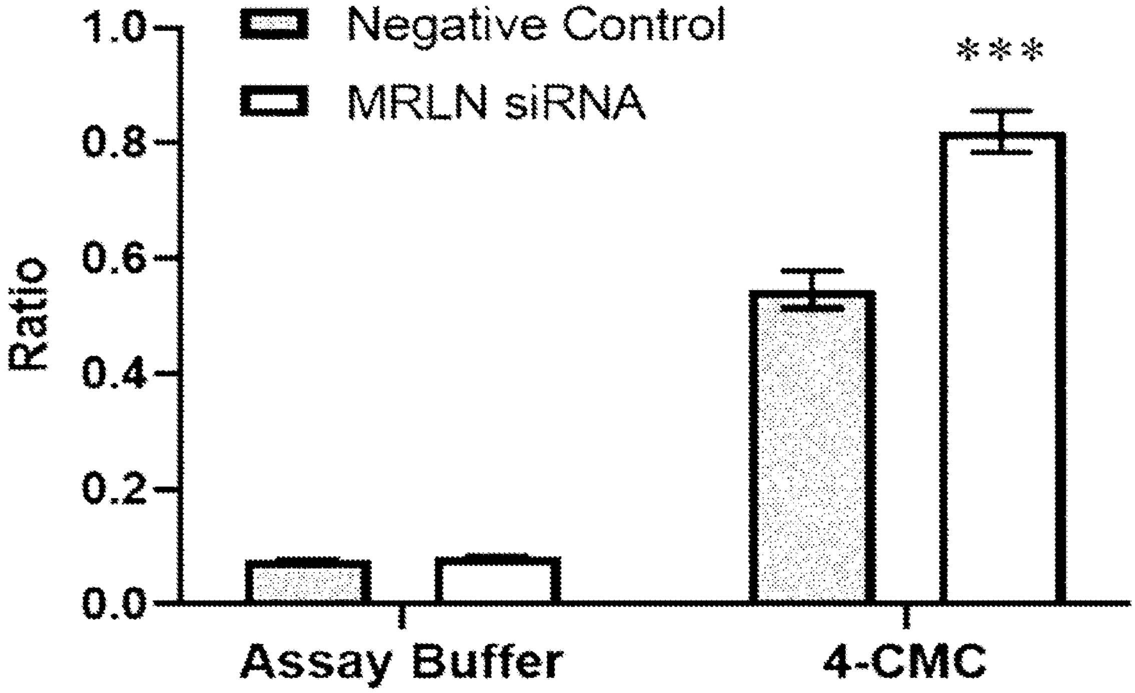
FIG. 4 A graph showing results of comparing a 4-chloromethcathinone (CMC)-dependent increase in calcium concentration when an MRLN-specific siRNA is added in cells derived from a DMD patient to that when a negative control is added.

DMD patient-derived cells (NCNP Muscle Repository) were seeded in a 384-well plate and cultured, and then, differentiation induction into myotubes was performed. After differentiation into myotubes, Lipofectamine RNAiMAX Transfection Reagent (invitrogen) and RNAi Silencer Select siRNA (Thermo Fisher) as siRNA against a human MRLN nucleobase sequence (SEQ ID NO: 3) or Silencer Select Negative Control No. 1 siRNA (Thermo Fisher) as a negative control were mixed, and then added to the cells, and the cells were further cultured in a $CO_2$ incubator. After culturing for 7 days, a medium was removed from the cells, a loading dye containing Cal-520 (AAT Bioquest) was added, and the cells were cultured for 1 hour at room temperature, and then, fluorescence values were measured at 1 second intervals for 10 minutes using an FDSS7000EX (Hamamatsu Photonics) at an excitation wavelength of 480 nm and a detection wavelength of 540 nm. Fluorescence values were measured for 1 minute and used as a baseline. One minute after the measurement was started, a ryanodine receptor agonist 4-Chloromethcathinone (CMC: Kanto Kagaku) was added to have a final concentration of 1 mM, and the measurement was further continued for 9 minutes. A value obtained by subtracting the baseline from a maximum value of an increase in fluorescence value due to an increase in intracellular calcium concentration was calculated, and the value was analyzed as a sarcoplasmic reticulum calcium level. The results are shown in FIG. 4. Due to the siRNA treatment, an amount of calcium released from sarcoplasmic reticulum was increased, suggesting that the MRLN knockdown by siRNA increased the sarcoplasmic reticulum calcium level.

The invention claimed is:

1. A method for treating muscular dystrophy, comprising: administering an effective amount of a myoregulin inhibitor to a subject in need thereof, wherein the myoregulin inhibitor includes an antisense oligonucleotide consisting of 10 to 50 bases and comprising a nucleobase sequence of at least 8 contiguous bases such that the nucleobase sequence is 100% complementary to an equal length portion of a nucleobase sequence of myoregulin.

2. The method according to claim 1, wherein the antisense oligonucleotide is consisting of 15 to 30 bases.

3. The method according to claim 1, wherein the nucleobase sequence of myoregulin is SEQ ID NO: 1 or SEQ ID NO: 3.

4. The method according to claim 1, wherein the nucleobase sequence of myoregulin is a nucleobase sequence having an identity of 90% or more with SEQ ID NO: 1 or SEQ ID NO: 3.

5. The method according to claim 1, wherein the muscular dystrophy is Becker muscular dystrophy.

6. The method according to claim 1, wherein the muscular dystrophy is Duchenne muscular dystrophy.

7. The method according to claim 1, wherein the muscular dystrophy is sarcoglycanopathy.

8. The method according to claim 1, wherein the antisense oligonucleotide is a modified oligonucleotide comprising a 5-methylcytosine.

9. The method according to claim 1, wherein the antisense oligonucleotide is a modified oligonucleotide including at least one nucleoside comprising a modified sugar.

10. The method according to claim 9, wherein the modified sugar has a bicyclic sugar.

11. The method according to claim 9, wherein the modified sugar has a substituted sugar moiety.

12. The method according to claim 1, wherein the antisense oligonucleotide is a modified oligonucleotide comprising a modified internucleoside linkage.

13. The method according to claim 1, wherein the antisense oligonucleotide is a modified oligonucleotide including at least one nucleoside of formula (1)

(I)

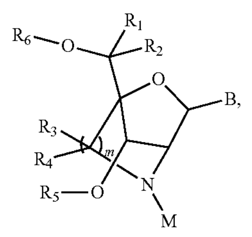

wherein B is a nucleobase, each of R1, R2, R3 and R4 is independently a hydrogen atom or a C1-6 alkyl group, each of R5 and R6 is independently a hydrogen atom, a protecting group of a hydroxyl group, a phosphate group, a phosphorus moiety, or a covalent attachment to a support, m is 1 or 2, and M is a sulfonyl group substituted with a methyl group.

14. The method according to claim 1, wherein the myoregulin inhibitor is administered orally to the subject in need thereof.

15. The method according to claim 1, wherein the myoregulin inhibitor is administered parenterally to the subject in need thereof.

16. The method according to claim 1, wherein the myoregulin inhibitor is administered daily in a range of 0.1 ng to 1000 mg per 1 kg body weight per dose.

17. The method according to claim 1, wherein the myoregulin inhibitor is administered daily in a range of 1 ng to 100 mg/kg/week.

18. The method according to claim 1, wherein the myoregulin inhibitor is administered in a range of 1 to 10 times per month.

19. The method according to claim 1, wherein the subject in need thereof is a patient in need thereof.

20. The method according to claim 1, wherein the nucleobase sequence of myoregulin is a nucleobase sequence having an identity of 95% or more with SEQ ID NO: 1 or SEQ ID NO: 3.

* * * * *

SEQUENCE LISTING

```
<160> NUMBER OF SEQ ID NOS: 4

<210> SEQ ID NO 1
<211> LENGTH: 446
<212> TYPE: DNA
<213> ORGANISM: Mus musculus
<220> FEATURE:
<221> NAME/KEY: CDS
<222> LOCATION: (231)..(368)

<400> SEQUENCE: 1

agtgagcttt tcgtccatgg agagcagatg gtgtttttga aaggaagggc ggccattccc      60

aggactttgg acttggctcc gttgcacccc tgaacagaac caacgttgct aggagaacac     120

ctgtgcccca gcactttggt ccagcaaggg caggagagga gagctggaaa ctggtagagc     180

tgtgctacct gctacctcct gaggctctca gggagcagga gaatctgaac atg agt        236
                                                       Met Ser
                                                       1

ggc aag agc tgg gta ctg atc tct act act tcg ccc cag agc ctg gaa       284
Gly Lys Ser Trp Val Leu Ile Ser Thr Thr Ser Pro Gln Ser Leu Glu
        5                   10                  15

gat gag att ctg gga cgg ctt ctg aaa att ctc ttc gtt ttg ttc gtt       332
Asp Glu Ile Leu Gly Arg Leu Leu Lys Ile Leu Phe Val Leu Phe Val
    20                  25                  30

gac tta atg tcc att atg tat gtc gtc ata acg tcc tagcaacctg            378
Asp Leu Met Ser Ile Met Tyr Val Val Ile Thr Ser
35                  40                  45
```

-continued

```
actttcttta ctccgtgtgt aagtttcaaa ccaaatgcga gcaaataaag atctacattt    438

taatctga                                                             446


<210> SEQ ID NO 2
<211> LENGTH: 46
<212> TYPE: PRT
<213> ORGANISM: Mus musculus

<400> SEQUENCE: 2

Met Ser Gly Lys Ser Trp Val Leu Ile Ser Thr Thr Ser Pro Gln Ser
1               5                   10                  15

Leu Glu Asp Glu Ile Leu Gly Arg Leu Leu Lys Ile Leu Phe Val Leu
            20                  25                  30

Phe Val Asp Leu Met Ser Ile Met Tyr Val Val Ile Thr Ser
        35                  40                  45


<210> SEQ ID NO 3
<211> LENGTH: 857
<212> TYPE: DNA
<213> ORGANISM: Homo sapiens
<220> FEATURE:
<221> NAME/KEY: CDS
<222> LOCATION: (349)..(486)

<400> SEQUENCE: 3

agaccagtga gcctcctgat ccaccaagac catatggtgt ttttcataaa agagagagat     60

cattcccttg actttggact tcgcttattg aacccctgga caacggaatc tccctctgtc    120

gcccaggctg gagtgcagtg gcaccatctc ggcttaccgc aacctccgcc tcctgggttc    180

aaacaatact cctaccttgg cctcctgagt agctgggatt acaggaatca aggttgctaa    240

gagaccacct gtgctgaata cactttgttc tggcaagagc agaaaactga gaagccgtgt    300

tacctaccac tacctgggat taattcaggg agcgggataa ttctggat atg act ggt     357
                                                     Met Thr Gly
                                                     1

aaa aac tgg ata tta att tct act act act ccc aaa agt cta gaa gat      405
Lys Asn Trp Ile Leu Ile Ser Thr Thr Thr Pro Lys Ser Leu Glu Asp
    5                   10                  15

gaa att gtg gga aga ctt cta aaa att ttg ttt gtt atc ttt gtt gac      453
Glu Ile Val Gly Arg Leu Leu Lys Ile Leu Phe Val Ile Phe Val Asp
20                  25                  30                  35

tta att tct att ata tat gtt gtg ata act tct tagaaagctg acttcctttc    506
Leu Ile Ser Ile Ile Tyr Val Val Ile Thr Ser
                40                  45

catgtacatt tcaaactgaa ttacagtgaa taaaaatttg tattttaact tgttgagtga    566

ctcacatttt atgacattgc caatttattc tagaagccaa caggacactg caatacaaac    626

aacattgtgt attgtttagt tctttatggt ttatgaaaca ttcacatata ctgaagtgaa    686

tttttttccc caaaaacatc tatcctactg agtcatgaaa cttctagatt tttagccagg    746

tgtggtggct cacacctgta atcccagcac tttgagaggc ccaggtaggc ggatcccttg    806

agtgcaggag ttcgatacgg gcctgagcaa cctgaagaaa tcccatctct a             857


<210> SEQ ID NO 4
<211> LENGTH: 46
<212> TYPE: PRT
<213> ORGANISM: Homo sapiens

<400> SEQUENCE: 4

Met Thr Gly Lys Asn Trp Ile Leu Ile Ser Thr Thr Thr Pro Lys Ser
```

-continued

```
1               5                   10                  15

Leu Glu Asp Glu Ile Val Gly Arg Leu Leu Lys Ile Leu Phe Val Ile
            20                  25                  30

Phe Val Asp Leu Ile Ser Ile Ile Tyr Val Val Ile Thr Ser
        35                  40                  45
```